United States Patent
Wente et al.

(10) Patent No.: US 12,221,599 B2
(45) Date of Patent: Feb. 11, 2025

(54) INCUBATOR, SYSTEM AND METHOD FOR MONITORED CELL GROWTH

(71) Applicant: Eppendorf SE, Hamburg (DE)

(72) Inventors: Wolf Wente, Hamburg (DE); Christoph Jolie, Hamburg (DE)

(73) Assignee: EPPENDORF SE, Hamburg (DE)

( * ) Notice: Subject to any disclaimer, the term of this patent is extended or adjusted under 35 U.S.C. 154(b) by 246 days.

(21) Appl. No.: 16/614,342

(22) PCT Filed: May 14, 2018

(86) PCT No.: PCT/EP2018/062350
§ 371 (c)(1),
(2) Date: Nov. 15, 2019

(87) PCT Pub. No.: WO2018/210734
PCT Pub. Date: Nov. 22, 2018

(65) Prior Publication Data
US 2020/0148993 A1    May 14, 2020

(30) Foreign Application Priority Data
May 15, 2017    (EP) .................................. 17171182

(51) Int. Cl.
*C12M 1/00*    (2006.01)
*C12M 1/34*    (2006.01)
*C12M 1/36*    (2006.01)

(52) U.S. Cl.
CPC ............ *C12M 41/14* (2013.01); *C12M 41/36* (2013.01); *C12M 41/48* (2013.01)

(58) Field of Classification Search
CPC ...... C12M 41/14; C12M 41/34; C12M 41/36; C12M 41/48
See application file for complete search history.

(56) References Cited

U.S. PATENT DOCUMENTS

| 11,360,107 B1 * | 6/2022 | Young ................ G01N 35/1016 |
| 2012/0244519 A1 | 9/2012 | Olesen et al. |
| 2013/0038727 A1 | 2/2013 | Clark |
| 2013/0280748 A1 | 10/2013 | Gebetsroither et al. |

(Continued)

FOREIGN PATENT DOCUMENTS

| EP | 1944358 A1 | 7/2008 |
| EP | 2484750 A1 | 8/2012 |
| JP | 2007-222083 A | 9/2007 |

(Continued)

OTHER PUBLICATIONS

Moscelli et al. "In incubator live cell imaging platform", Proc. of SPIE, vol. 8066, pp. 1-8.

(Continued)

*Primary Examiner* — Lydia Edwards
(74) *Attorney, Agent, or Firm* — Todd Lorenz

(57) ABSTRACT

The invention relates to an incubator, a system and a method for the monitoring of the growth of cells in a cell culture by acquiring cell monitoring data in the incubator. The incubator comprises a data storage device (4a) and a data processing device (4b) that are configured to acquire at least one incubator chamber value and at least one cell growth value in form of cell monitoring data and to store the cell monitoring data in the data storage device.

14 Claims, 3 Drawing Sheets

(56) References Cited

U.S. PATENT DOCUMENTS

2014/0271571 A1    9/2014   Magnant

FOREIGN PATENT DOCUMENTS

| | | |
|---|---|---|
| JP | 2009-247261 A | 10/2009 |
| JP | 2010-158185 A | 7/2010 |
| WO | WO 2007/052716 A1 | 5/2007 |
| WO | WO 2011090792 A1 | 7/2011 |
| WO | WO 2016161163 A2 | 10/2016 |
| WO | WO-2016161174 A1 * | 10/2016 ............ C12M 23/16 |

OTHER PUBLICATIONS

Qiuli et al., "Design of monitoring system of temperature and humidity in tissue culture room", Electronic Test, vol. 16, pp. 31-32.

* cited by examiner

INCUBATOR, SYSTEM AND METHOD FOR MONITORED CELL GROWTH

This invention relates to an incubator for the monitored growth of biological cells. Furthermore, the invention relates to a system and a method for the monitored growth of biological cells.

In biological and medical laboratories, cells are kept in cell culture under controlled environmental conditions within such incubators, and by this the growth of living cells in vitro is rendered possible. To this goal the temperature and the composition of the gas, resp. the air humidity of the atmosphere inside an incubator chamber, which is isolated from the surrounding, is regulated by technical appliances of the incubator to the desired values. Eukaryotic cells require $CO_2$ incubators. The atmosphere is formed of air with a defined concentration of $CO_2$ and $O_2$ and a defined humidity, in many cases a suitable temperature is 37° C.

Cells are required for a broad spectrum of applications in biology, medicine and pharmacy. It is of importance for these applications that the cells are provided with desired properties, that is in a reproducible manner. Immortalized cell lines offer particularly suitable conditions for these prerequisites, as they can provide a genetically uniform cell type, and a virtually infinite number of cell division cycles is possible, as well as the possibility of freezing (and thawing) in a long-term storage regulated to a temperature of −196° C.

The growth of cells depends critically on the environmental conditions in the incubator. Therefore, the incubator chambers are periodically subjected to cleaning and disinfecting procedures. Additionally, incubators are equipped with particularly high-grade electronics and sensors. Commonly, the sensors are calibrated on a regular basis. However, in practice it occurs eventually that despite a seemingly accurate adherence to the necessary maintenance protocols the growth of the cells does not exhibit the expected results. This is true even for immortalized cell lines.

In order to gather information about the growth process, the cell cultures, resp. the cells, are oftentimes removed temporarily from the incubator for a visual inspection and a morphological control as well as for counting the cells. These measures provide snap shots that could be useful for evaluation of the of the cell growth up to that moment. However, such measures interrupt the growth of the cells and disturb it by agitating the cell medium and by the at least temporarily exposure to the atmosphere of the laboratory. A reliable continuation of the development of the so-controlled cells is questionable. Furthermore, the removal of a cell culture vessel from the incubator also leads to a disturbance of the other cell cultures inside the incubator due to the disturbance of the atmosphere inside the incubator that occurs when opening the door of the incubator.

Accessories for monitoring cell cultures that can be placed in the incubators are known. With these accessories certain information about the growth of a cell culture can be gathered on an external computer without having to remove the cell cultures from the incubator chamber. This allows the user on the computer to be informed about the state of the cell culture growth via the transmission of images and/or via image analysis. With such solutions, the overall high expenses of such systems appear less satisfactory, in particular in respect to the acquisition of the accessories and the incubator, its maintenance and the complexity of operating them. Furthermore, accessories are operated independently from the incubator, so that the user setting up the incubator or the accessories in an unsolicitous way could induce a malfunctioning or damaging of the instruments. E.g. it could occur that instruments that are sensitive to temperature were left inside the incubator chamber during a high temperature disinfection of the incubator, or respectively that instruments that are not sensitive to temperature were removed needlessly. Also, it could occur that temporarily unused accessories were left turned on and disturbed the climate.

The underlying task for the present invention is therefore to provide cells of a desired consistency in a more reproducible and more efficient manner.

The invention solves this task with the help of an incubator according to claim 1, the system for the data exchange according to claim 10, the system according to claim 11 and the method according to claim 12. The preferred embodiments are particularly subject to the dependent claims.

The incubator for the monitored growth of cell cultures according to the present invention consists of: an incubator chamber accepting at least one cell culture vessel, which contains a cell culture growing with that vessel, a sensing device for the measurement of at least one parameter of the chamber, which characterizes the physical state of the incubator chamber, in form of at least one first measurement value, at least one measurement device for the measurement of at least one growth parameter that characterizes the growth of the cells of this cell culture in form of at least one second measurement value, a data storage device, and a data processing device that is programmed to record the at least one first measurement value and the at least one second measurement value in form of cell monitoring data and to save the cell monitoring data in the data storage device.

In contrast to the known incubators the present incubator introduces a new category of apparatuses that serves as a central hub for information. It collects information about the growth of the cells in the individual incubator and by doing so it collects reference data that allow for a standardized approach for the cell culture in that incubator. The high-grade and precisely calibrated sensors of the incubators offer a foundation for the acquisition of a reliable set of data for the characterization of the cell growth in that incubator under its atmospheric conditions, in particular $CO_2$, $O_2$, relative humidity, and/or number resp. duration of the events of opening the doors. During that the internal parameters of the incubator, in particular the chamber parameters, together with the growth parameters measured by the measurement device, are collected, in order to allow for a determination of possible correlations between the values of the parameters and their changes. In this way, monitoring data of the cells can be collected, which then can be used as a reference for the estimation of the development of cell cultures growing in the incubator in the future. By simultaneously acquiring the environmental conditions of the incubator in form of a first measurement value as well as the growth parameters in for of a second measurement value and the storage of both measurement values these information are present in one unique device. The incubator, when functioning as a central hub for the information, could be connected to a network and could send, via this network, the data it has acquired to a database for storage. This database could be accessible either publicly or to a defined group of users. By making this data accessible it will be possible for the first time to collect information from multiple user on the growth of cells under the acquired environmental conditions, to make it accessible and also to document it. It is possible to connect these cell monitoring data with the acquired data on the environmental conditions of the incubator. By this, a standardization of the cell cultivation will become possible. Furthermore, it will be facilitated considerably to transfer the acquired data on the cells and on the environmental conditions from one work group to another, even on a global scale. This will enable for cooperations between users, which are supported on the basis of validated data and traceable results. With this, a possibility is created to render cell culture more reproducible. In particular, in the case of poor performance of the growth, the measurement values regarding the cell culture are not sufficient by themselves in order to analyze the causes. Now for the first time, it is possible to facilitate the cause analysis as now also the data on the chamber parameters, i.e. the data on the environmental conditions, is available and can flow into the cause analysis.

The interior of a closed incubator chamber and the designated parts within it form a physical system, which ideally is precisely controllable by the incubator. In particular the precise and preferentially calibratable sensing devices of the incubator serve to this aim. This closed system defines the environment in which the cell cultures live. The acquisition of the physical states of this closed systems therefor allows for a precise registration of the environmental conditions that influence on the live and growth of the cell cultures. This constellation offers ideal conditions for the use of the incubator as a central hub for the acquisition of data. One particular advantage of this constellation is that precise data on all actions and processes regarding the incubator chamber that have been controlled, and particularly initiated by the incubator, resp. its electronic control device are available.

One particularly relevant action that is controlled by the incubator or at least preferentially recorded by a sensor in the incubator is the opening and/or closing of a door of the incubator, in particular of a chamber door of the incubator chamber. Preferentially, the sensing device is configured to record the opening and/or closing of the door of the incubator as a chamber parameter, as this is in particular a matter of the physical state of the incubator chamber. Preferentially this chamber parameter is saved with a time-tag. The information "door open and/or "door closed", in particular when being time-dependent, can be saved in form of values of a corresponding parameter of the incubator door. According to experience, the opening of the incubator door and the corresponding alternation of the atmosphere inside the incubator chamber influence strongly on the growth of the cells, in particular if this occurs repeatedly—as in practice it is likely to happen for an incubator that hosts several cell cultures. Therefore it is particularly useful to correlate the parameter of the incubator door with a growth parameter, in particular if both parameters are stored time-dependently. The parameters of the chamber are in particular the atmospheric conditions inside the incubator chamber, in particular CO2, O2, N2, relative humidity, and/or number and duration of the events of opening the doors.

The processes controlled by the incubator itself include all steps of the temperature control, that influence on the physical state "temperature of atmosphere in the incubator", in particular also step of the automatized disinfection via periods of high temperature at ca. 100° C. to 120° C. or up to 180° C. or 200° C., that will be applied when the incubator chamber is empty. The incubator, resp. its controller is preferentially configured to store in the data on the cell monitoring the set temperature applied to a control circuit for the temperature at a defined moment or the temperature values that have been detected as a result of the temperature control.

Among the processes that are controlled by the incubator itself could also be processes of gas exchanges. In these processes parts of the incubator atmosphere are exchanged according to a volume flow with a predefined volume per time, in particular as a part of a controlling event for regulating the desired composition of gases in the incubator atmosphere, in particular if this composition has been altered in an unwanted way. In this case the corresponding physical state that has to be measured is the relative concentration of the gases and the relative humidity. The incubator, resp. its control device is preferentially configured to store in the data on the cell monitoring the relative gas concentration that has been applied as a set value of a control circuit for the temperature at a defined moment or the values detected as a consequence of a relative gas concentration, in particular $CO_2$ and/or $O_2$ values. This control of the gas also comprises the control of the air humidity that is carried out by a humidity sensor of a sensing device, in particular by a sensor for the measurement of the relative humidity.

Among the processes that are controlled by the incubator itself could also be processes of gas circulation. In these processes, as an example, parts of the incubator atmosphere will be moved in the incubator chamber according to a volume flow with a predefined volume per time and in particular also in one or several variable or constant directions of flow. In particular, this can result in a more homogeneous atmosphere within the incubator chamber, so that in particular differently positioned cell culture vessels are exposed in the time average to the same atmosphere.

The measurement device is configured to measure at least one growth parameter that characterizes the growth of the cells of this cell culture. The growth parameter can be the pH value of the cell medium of the cell culture if the measurement device comprises at least one pH detector with which the pH value of the medium can be measured or estimated. The pH detector can be non-invasive, when it relies for example on an optical measurement of the cell medium, in particular on a recognition of the color of the cell medium. Cell media are provided with pH dependent dyes in order to allow for a visual inspection of the pH value. This circumstance can be used in the described manner also for an optical device-based measurement.

The growth parameter can describe the number of cells in a test area of the cell culture vessel if the measurement device is equipped with a cell counting device. For this the measurement device comprises preferentially an image recording sensor, e.g. a CMOS sensor, with which an image or a film of the cells to be counted is recorded. An image is preferentially understood as a set of data composed of data that contains in particular values of light intensities that have been recorded by the light sensitive elements of the image recording sensor. In the framework of the present invention an image can, but does not have to mandatory, refer to an optical representation, in particular a representation of a cell culture. An image can then be analyzed by a software-based image recognition that is integrated preferentially as a component into the incubator or the system according to the invention, in particular via particle recognition and counting. Furthermore, at least one device for influencing on the light emitted from the light source and/or the light captured by the sensor can be provided as a component of the measurement device. By means of the optics a reflected-light microscopy can be realized, in particular a phase-contrast or dark-field microscopy.

The growth parameter can describe the confluence of the cell layer in the cell culture vessel, i.e. the density of cells. For this, the measurement device is configured preferentially as a confluence measurement device. To this aim the measurement device comprises preferentially an optical sensor, and preferentially a light source as a component of the measurement device. The radiation of the light source preferentially captures the cell culture and in particular it is directed towards it. Furthermore, at least one means for influencing on the light irradiated from the light source can be provided as a component of the measurement device. Those means are selected from the group of preferred means, comprising a lens, a prism, an optical filter, a mirroring element, a light transmitting fiber. By means of the optics, a reflected-light microscopy can be realized, in particular a phase contrast- or dark field microscopy. This sensor is preferentially a sensor with a spatial resolution, e.g. a CMOS-sensor or a camera. With such a sensor, in particular an image of the cell layer can be acquired. This image can then be evaluated by a software-based image analysis, in particular via a detection of can and a counting of the shapes enclosed by the edges that can be interpreted as cells of the cell layer.

The measurement device can also be configured to carry out the confluence by an electric measurement of the cell layer of the cell culture, in particular with at least one measurement of the electric resistance, resp. the impedance of the growing cell layer, in particular by time-resolved measurements. The cell-layer represents a capacitance, and this fact can be exploited for its characterization. To this aim, the cell culture vessel comprises preferentially one electrode, in particular a planar electrode, above with the cell layer is forming. This electrode is designed so that it can be electrically connected with the measurement device of the incubator. Such measurement technique is known in particular under the term impedimetry resp. ECIS (electric cell-substrate impedance sensing)

Different methods for the determination of the state of the confluence of the cell layer on the substrate of a cell culture vessel could comprise to label the cells radioactively, and/or to label the cells with cell dyes and observe them with reflected light microscopy, in particular a phase contrast microscopy or dark field microscopy. Also, fluorescence microscopy is viable for the analysis of the confluence. In this case, the cells are labeled with fluorescence-labeled proteins or particles and are rendered visible by this process.

The growth parameter can also describe the morphology of the cells of the cell layer. The morphology of the cells can be characteristic for difference stages of the growth of the cell—non-adherent cells in suspension are in most cases spherically shaped and when they adhere to a planar substrate they flatten and adopt a mostly planar shape of the side facing the substrate. The morphology of the cells can be characteristic for a cell type, resp. cell line and can be identifiable by a measurement of the morphology. The morphology of the cell can also describe an apoptotic or necrotic state of the cell, which can be identifiable by a measurement of the morphology.

Therefore, the measurement device is constructed preferentially as a device for morphology measurements. To this aim the measurement device comprises preferentially an optical sensor, and preferentially a light source as a part of the measurement device. The radiation of the light source preferentially captures the cell culture and, in particular, it is directed towards the cell culture. Furthermore, at least one means for influencing on the light irradiated from the light source and/or on the light captured by the sensor can be provided as a component of the measurement device. Those means are selected from the group of preferred means, comprising a lens, a prism, an optical fiber, a mirroring element, a light-transmitting fiber. By means of the optics, a reflected-light microscopy can be realized, in particular a phase contrast or a dark field microscopy. The sensor is preferentially a sensor with a spatial resolution, e.g. a CMOS sensor or a camera. With such a sensor, in particular an image of the cell layer can be acquired. This image can then be evaluated by a software-based image analysis, in particular via a detection of edges and a counting if the shapes enclosed by the edges that can be interpreted as cells of the cell layer.

The measurement device preferentially comprises an analog digital converter in order to digitize the at least second measurement value and to provide it as cell monitoring data. Therefore, the measurement device comprises preferentially one (own) data processing device, in particular a micro processor, which particularly will be termed also second data processing device, and preferentially a proper data storage device, which particularly will be termed also second data storage device. The measurement device is preferentially configured to measure at least the second measurement value, independently of the data processing device of the incubator, resp. it is configured to control the execution of the measurement, in particular according to an own control program (second control program) that is executed by the second data processing device.

It is also possible and particularly preferred to have the data processing device of the incubator (first data processing device) control the execution of the measurement of at least a second measurement value. By this, a low-energy and efficient acquisition of cell monitor data can be realized. At the implementation one has to respect that the operation of electric device inside the incubator chamber could possibly generate waste heat, which heats the chamber atmosphere to an unacceptable degree. Therefore, the control device of the incubator can particularly be configured to control the operation of the electric devices, in particular at least of the one measurement device and/or a handling device inside the incubator chamber in function of the temperatures of the chamber atmosphere that are recorded by temperature sensors. The control device of the incubator can in particular be configured to control the heat flow in the chamber atmosphere with the at least one temperature control device and by operating the electric devices inside the incubator chamber in reciprocal dependence in order to compensate for the unwanted heating of the chamber atmosphere.

The acquisition of the first and second measurement values and/or the storage of them is carried out preferentially under the control of the data processing device, resp. the control device of the incubator, in particular according to the specifications of a monitoring program. The monitoring program can be part of the control program of the incubator, in particular it can be a subprogram.

The data processing device is preferentially part of the control device of the incubator that controls the functions of the incubator. The functions of the control device are implemented in particular as electronic circuits. The control device can comprise a microprocessor that can contain the data processing device. The control device and/or the data processing device is preferentially designed for the execution of a controlling method that is also termed as control software or control program. The functions of the incubator and/or of the control device can be described as procedural steps. They can be realized as part of the control program, in particular as subprograms of the control program.

In the framework of the present invention, the control device generally comprises in particular the data processing device, in particular a calculating device (CPU) for the processing of the data and/or a microprocessor or the control device is the data processing device. The data processing device of the control device of the incubator is preferentially also configured to control a handling process and/or individual handlings that are executed by one or several in particular optional handling devices of the incubator.

The data processing device is alternatively an apparatus that is preferentially located on the outside of the incubator and arranged separately from it, also termed as an external apparatus resp. external data processing device. The data processing device and the incubator preferentially have established a data communication and are preferentially part of a network for the exchange of data. In this case, the data processing device and the incubator are in particular constituent parts of a system for the monitoring of the growth of cell cultures according to the present invention Here, such constituent parts of a network are also termed network instruments. Also the at least one measurement device can be configured as a network instrument. The network for the exchange of data is preferentially an essentially non-hierarchical network, in particular a network whose constituents, i.e. the network instruments, form at least in part or all a peer-to-peer network architecture. In a peer-to-peer network all constituents have equal rights and can make use of services as well as offer such services. The network for the exchange of data preferentially uses a ethernet technology or is preferentially an ethernet network.

The system, the incubator and/or the control device and/or the data processing device and/or at least one measurement device are preferentially configured to acquire the cell monitoring data according to at least one of the following configurations:
  Cell monitoring data are acquired at instants of time according to a predefined schedule that can be defined by the incubator and/or influenced or defined by the user via a user interface device of the incubator; such information about the instant of time can contain information about the absolute date and time that will be used by the incubator by comparison with the data of an optionally available or preferentially available clock.
  The cell monitoring data is acquired at specified time intervals, in particular at regular time intervals, e.g. time intervals dt=10 minutes to 20 minutes etc. The time intervals can be defined by the incubator and/or influenced or defined by the user via a user interface device of the incubator.
  Cell monitoring data are acquired in function of at least one specified event that is preferentially selected from the group of the following events:
    a measurement value that has been measured by the sensing device complies with a specified condition, e.g. an illicit deviation from the set temperature (37° C.) in the incubator chamber that was caused by e.g. an open door of the incubator, or an illicit deviation of a relative gas concentration in the incubator chamber, in particular a $CO_2$ and/or $O_2$ value and/or $N_2$ value; a typical $CO_2$ value in incubator chambers is 5%;
    an error condition that has be identified by the incubator, regarding hardware or software;
    a control signal is received via a communication device of the control device of the incubator or of the measurement device that triggers the acquisition of cell monitoring data; such control signal can in particular be prompted by an external data processing device or by an user input.
  A control program that is executed by the data processing device or by the control device of the incubator triggers a measurement of the cell monitoring data after an analysis method employed by the control program had analyzed previously measured second measurement values; in this the analysis program can provide the triggering of the measurement of cell monitoring data due to a condition selected from the group of the following conditions:
    At least one previously measured second measurement value deviates from at least one reference value or lies outside of a predefined range;
    At least one trend of two or many previously measured second measurement values deviates from a reference trend or lies outside of a predefined reference range; this reference trend or reference range can be a known standard trend or standard range that in particular can depend on different parameters, in particular on the information about the cell type and/or the cell medium used for the cell culture in question.

The system, the incubator and or the control device and/or the data processing device and/or at least one measurement device are preferentially configured to acquire the cell monitoring data in function of cell identification data. Cell identification data can be supplied beforehand by the user e.g. via a user interfacing device of the incubator. The incubator or the system can also comprise an identifying device for the recognition of a cell culture vessel or of a cell culture. In particular, correlation data, information about the correlation consisting of cell identification data and a previously established marker, can be available to the incubator. The marker can be attached to the cell culture vessel and can be machine-readable by a reading device of the incubator or of the system. The marker can be a code, in particular a bar code, a two dimensional code, or a machine-readable character or sequence of characters.

By the acquisition of cell monitoring data in function of cell identification data a data pool in function of the cell type, in particular of a cell line can be generated and stored. In this way, it is possible to acquire the history of the growth of a particular sample of cells, resp. sample of a cell line and their subcultures obtained by splitting. An electronic cell file with the historic growth data can be recorded.

Independently of the development of a single sample of cells, resp. sample of a cell line that has been possibly split, frozen and thawed again, also the growth behavior of a cell type resp. a type of cell line can be traced by repeatedly acquiring cell monitoring data of this cell type resp. type of cell line from several individual cell samples resp. samples of cell lines, preferentially in function of the used individual incubator, a production series of an incubator, a type of incubator or other information. In the system according to the present invention, this acquisition can be carried out particularly from incubators distributed regionally or globally, resp. nationwide or worldwide. In this way, an electronic cell file can be generated from these historic types of growth in reference to a cell type resp. a type of cell line. From this valuable reference data and correlated information can be deduced, in particular one can define standard trends and standard ranges that in turn can be used by the incubator or system according to the present invention.

Correlated information can e.g. comprise in how far a certain cell line exhibits a characteristic growth dynamics that is varied after a certain number of splitting events as compared to the growth dynamics before the splitting, resp. in how far growth behavior depends on the number of splitting events. Correlated information can e.g. also comprise how the growth behavior of a certain cell line depends on the number of events of opening the incubator door or on the total duration of the incubator door being open or on other statistical information about the opening of the incubator door. Correlated information can e.g. also comprise how the growth behavior of a certain cell line depends on the number and/or type of changes of the growth medium of the cell culture. Correlated information can e.g. also comprise how the type of cell culture vessel, in which the cells are growing, influences on the growth behavior. To this aim, the incubator could acquire from the user information about the type of cell culture vessel used or an individual identification number of the cell culture vessel via the acquisition of the data on the cell culture vessel in a user interface. Also, an ordering- or batch number can be acquired with the other data. Thus, it can be in particular traced back whether the growth surface of the cell culture vessel or of the type or of a production batch of this type worked flawlessly.

In particular, at least one control parameter that influences on the control method can be assigned by the incubator or system according to the present invention in function of such reference data. This influence can consist in the control method outputting, in function of the control parameter, an information to the user via the user interface device on when the cell culture vessel needs to be removed from the incubator so that a certain growth parameter, e.g. adhesion of the cells, number of cells in the vessel, density of cells, morphology, is existent as desired by the user.

The system, the incubator and/or the control device and/or the data processing device and/or at least one measurement device is configured to use the cell monitoring data for the generation of electronic documentation file, in which the growth of an individual cell sample in a cell culture vessel or the growth of several cell cultures in cell culture vessels is logged and documented. This documentation file is then stored on the data storage device. As the cell monitoring data can allow for deductions on the environmental conditions, it can, on the one hand, be certified that certain standard protocols for the cultivation of cells have been followed. On the other hand, deviations from such standard protocols can be identified later and/or correlated information can be determined. By the acquisition of such data the quality of the cell-based laboratory works, resp. the medical, biological, and pharmaceutical processes, can be improved significantly and can be rendered more reliable. The reproducibility of cell-based laboratory works can be enhanced, deviations from standard properties can be detected early in order to give the user the possibility of a correction or an early repetition of the experiment. The documentation file can be made available to the user or to an external data processing device by the control device through a data exchange. In particular in critical applications, which could e.g. have a forensic relevance or in which cells of a considerable value are cultivated, such documentation is particularly sensible.

The invention serves in particular to the aim of achieving a standardization of the growth behavior of the cells in cell culture, in order for the user to obtain the growth result that he desires, in particular for a specified cell adhesion, as e.g. after the thawing of cells, number of cells in cell culture, cell density and/or morphology of the cells, each respectively also termed as a growth goal. This is achieved in particular by recording the dependence of the cell growth on the first measurement value and/or the second measurement value, in particular on cell monitoring data. The cell growth is represented particularly by at least one growth parameter. In particular, the temporary recording of the second measurement values can be used using a planning program for achieving the growth goal. The incubator according to the present invention serves as a tool for the harmonization (standardization) of the approach to reaching a desired growth parameter in cell cultures. The cell monitoring data serve as a data foundation, with which correlations of cell monitoring data, in particular of first and second measurement values can be determined (correlated information) or causal relationships between cell monitoring data, in particular in function of a cell type, in particular a cell line. As an example, it can be determined how a growth parameter depends on the parameter of the incubator door. The so-determined correlation or the so-determined relationship can assessed for the definition of a planning program for a cell culture. As an example, it can be determined that—in particular for a certain cell type—the cell confluence after the spreading of the cells and/or the beginning of the incubation is dependent on a certain number of opening events of the incubator door in a define period after the spreading of the cells and/or the beginning of the incubation, in particular that the cell growth is slowed down by that opening events of the door. It can, for example, be deduced from this relationship that the user can expect the reaching of the desired confluence only after a certain moment after the spreading of the cells and/or the beginning of the incubation that is calculated by the incubator on the basis of the known correlations.

The incubator and/or the control device and/or the data processing device are preferentially configured to execute at least one processing step in function of cell monitoring data. This arrangement broadens the functionality in a beneficial way. In a preferred embodiment this processing step comprises to output an information about the cell monitoring data to the user via the user interface device or to store cell monitoring data in a data processing device.

Preferentially, the control program of the incubator or of the system or of an external data processing device comprises a planning program, in particular a time planning program with which a growth plan can be calculated in form of planning data in function of cell monitoring data. This growth plan can calculate at least one growth parameter using the cell monitoring data, in particular the temporal evolution of that growth parameter. It can also calculate the instant of time or period of time, at which/after which a growth parameter fulfills a specified condition, e.g. a specified value. This growth parameter can be in particular: a cell adhesion (e.g. the fraction of cells in the cell culture vessel that have adhered to the substrate of the cell culture vessel), a number cells present in the cell culture vessel after cell divisions, a cell density (number of cells per area of the substrate present in the cell culture vessel after cell divisions), doubling time, or cell morphology (e.g. statistical information about the cells present in cell culture vessel with certain morphological properties as the absolute substrate area covered by a cell, form and outline—e.g. similarity to a spherical shape, height in the vertical distance to the substrate etc., to be evaluated in particular each with a image acquisition and image analysis). The growth parameter can also comprise the pH-value of the cell culture medium, which was determined e.g. with a measurement of the optical absorption.

In particular, by means of the planning program, it can be calculated when the electronic access denial device of the incubator automatically prohibits the access of the user to at least one function of the incubator. An incubator door as a access denial device can in particular comprise an electronically addressable lock, with which the opening of an incubator door is prohibited. This access denial device can in particular be part of a control program, by which a software-controlled function of the incubator can be activated/deactivated. In this manner, the growth of the cell culture in the incubator can be protected from atmospheric disturbances during delicate phases.

The control program of the incubator or of the system or of an external data processing device preferentially comprises at least one prediction algorithm for calculating at least one growth parameter using the cell monitoring data, in particular the temporal evolution of that parameter. The prediction algorithm describes preferentially that the known standard evolution of a growth parameter varies in function of the cell monitoring data.

The process step that is executed in function of cell monitoring data can be preceded by a comparison of the cell monitoring data with reference data as a part of the analysis method. This reference data can have been determined by the same incubator or can be transferred to the analyzing incubator through a data connection.

The process step that is executed in function of cell monitoring data can provide to output information, in particular regarding planning data, to the user via a user interface device or to send data, in particular planning data, to an external data processing device via a communication device of the incubator.

The process step that is executed in function of cell monitoring data can provide to carry out the control of at least one control parameter regarding the setting resp. the regulation of the atmosphere in the incubator chamber in function of the cell monitoring data. The process step that is executed in function of cell monitoring data can provide to carry out the control of a handling using a handling device in function of cell monitoring data.

Preferentially, the control method is configured to operate the incubator in function of cell monitoring data in such a way that a provided growth goal will be reached.

The incubator is a laboratory incubator and as such a device, with which controlled climatic conditions for different biological development- and growth processes can be generated and maintained. It serves in particular for the generation and maintenance of a micro climate with controlled gas, and/or humidity and/or temperature conditions in the incubator chamber, where this treatment can be time-dependent. The laboratory incubator, in particular a handling device of the laboratory incubator, can in particular comprise a timer, in particular a time switch, a heating/cooling device, and preferentially a regulation for the control of an exchange gas that is delivered to the incubator chamber, a regulating device for the composition of the gas in the incubator chamber of the incubator, in particular for the regulation of the $CO_2$ and/or the $O_2$ and/or the $N_2$ content of the gas and/or a controlling device for the regulation of the air humidity in the incubator chamber of the incubator. The incubator, in particular the handling device of the incubator, comprises in particular an incubator chamber, furthermore, preferentially a closed-loop control device with at least one control circuit, which has assigned as actuator at least one heating/cooling device and as measuring element at least one temperature measurement device. The temperature in the incubator can regulated using the control device. Depending on the embodiment, also the air humidity can be regulated with it. A water-filled trough can be heated or cooled in order to adjust the air humidity with the evaporation. $CO_2$ incubators serve in particular for the cultivation of animal resp. human cells. Incubators can comprise turnover devices for the turning of the at least one cell culture vessel and/or a shaking device for the shaking resp. moving of the of the at least one cell culture vessel.

The control device can be configured so that a program parameter of a control parameter of the incubator is selected automatically in function of cell monitoring data. A handling of the at least one cell culture in at least one cell culture vessel that is controlled by the control parameter corresponds in the case of an incubator in particular to a climate treatment to which at least one cell culture is subjected. Possible parameters, in particular program parameters, in particular user parameters that are used for influencing on a climate treatment define in particular the temperature of the incubator zone, in which the at least one sample is incubated, the relative gas concentration of $O_2$ and/or $CO_2$ and/or $N_2$ in the incubation space, the air humidity in the incubation space and/or at least one process parameter that influences on or defines the process, in particular the sequence, of an incubation handling program consisting of several steps.

A sensing device comprises in particular at least one temperature sensor, preferentially a multitude of temperature sensors. A temperature sensor can for example be a Pt 100 or a Pt 1000 temperature sensing element. A sensing device comprises preferentially one sensor for the determination of a relative gas concentration, in particular for the determination of the content of CO2 and/or O2 and or N2. A sensing device comprises preferentially a sensor for the determination of the relative air humidity.

The incubator chamber comprises chamber walls and at least one opening, through which the cell culture vessels can be placed or removed in/from the inside of the incubator chamber. This chamber opening can be closed with a closing element that is movably connected to the incubator chamber, in particular with a chamber door that is movably mounted to the incubator chamber using a hinge, in particular with one or several chamber doors. In the closed position of the chamber opening the inside of the incubator chamber is isolated from the surrounding preferentially in such a way that in the inside a desired atmosphere that is controlled by the incubator can be adjusted, in particular controlled. In the open position of the chamber opening an exchange of gases through this opening is possible between the surrounding of the incubator and the inside of the incubator chamber. Typically, the camber opening is located in the front wall of the incubator chamber.

The incubator chamber comprises preferentially several walls that can in particular be formed as single pieces and in particular be joined without edges. The walls are formed preferentially essentially planar, but they can also all or partially comprise a curved form. The incubator chamber is preferentially shaped as a cuboid, but can also be shaped differently, e.g. spherically, ellipsoidally, as a polyhedron. The walls are fabricated preferentially from a corrosion-resistant material, in particular stainless steel, copper, brass, or a plastic, in particular a composite plastic. By this, the cleaning/disinfection of the interior of the chamber is facilitated. Independently from the opening that serves for the loading/removal of cell culture vessels, the incubator chamber can comprise a port for feeding through a cable connection from the inside of the incubator chamber to its outside or in the surrounding of the incubator.

The incubator can comprise exactly one incubator chamber, but can also comprise several incubator chambers, where the atmosphere (temperature, relative gas concentration, air humidity) can be adjusted in particular individually or collectively. A typical size of the interior of an incubator chamber is in the range of 50 to 400 liter.

The incubator chamber can comprise a holding frame for holding one or several shelf sheet insets or insertable instruments. Alternatively or additionally, at least one of the interior walls of the incubator chamber can be configured to hold one or several shelf sheet insets or insertable instruments. To this aim a holding structure that is integrated into the wall can be provided, in particular one or several ledges, grooves, or racks. A shelf sheet inset increases the storage area in the incubator chamber. A instrument that can be inserted into the interior can be designed as a module and allows for the execution of automatized work steps in the interior, preferentially also with the closed incubator door. The holding frame is also preferentially fabricated of a non-corrosive material, preferentially stainless steel. The holding frame is laid-out as a standing object, by comprising at least one pedestal section that rests on the floor wall of the incubator chamber. But it can also be supported on the side walls of the incubator chamber and/or suspended from the ceiling wall of the incubator chamber.

The incubator can comprise a casing that encases the incubator chamber partially or completely. The casing can be designed essentially in the shape of a cuboid, and can be in particular designed so that the incubator is stackable.

Preferentially, the incubator comprises a handling device for handling of the at least one cell culture vessel. The term "handling" implies in particular that a cell culture of a cell culture vessel is moved, and/or transported, and/or investigated, and/or modified, in particular modified physically, chemically, bio-chemically, or in a different manner.

A handling device can be a moving device, with which the cell medium of at least one cell culture vessels can be kept in motion, preferentially by a moving program that is controlled by the control program. A moving device can be a shaking or a rocking device. The moving device comprises preferentially a carrier device, in particular a plate, upon which one or several cell culture vessels can be placed and/or fixated. A moving device comprises preferentially a driving device, in particular in the case of the shaking device oscillatory drive, with which the desired moving program can be implemented. The design of the moving program can depend on the growth state of the cells of a cell culture and can depend on the cell type, in particular on the cell line. The design and/or control of the handling, in particular of the moving program can depend on the cell monitoring data. The one handling device can be a rocking device, with which at least one cell culture vessel is rocked. The parts of a rocking device can correspond to those of the shaking device, but they are configured for the rocking movement.

The handling device can also be a transport device, with which at least one cell culture vessel can be transported in the incubator chamber. The transport device be a lifting device, comprising a mounting device, onto which the at least one cell culture vessel can be placed. The lifting device comprises preferentially a moving mechanism and/or an electrically addressable driving mechanism for driving the moving mechanism. The transport device can furthermore be a movable and electrically addressable arm and gripper for gripping and holding of at least one cell culture vessel. The transport device can comprise a conveyor belt for moving of the at least one cell culture vessel, which is placed upon it. By means of the transport, the at least one cell culture vessel can be moved in the incubator chamber, in particular to a work position in a work station in the incubator chamber, and away from this work position. The control device is configured to control the transport device in function of cell monitoring data.

A work station can comprise at least one measurement device for measuring at least one growth parameter that characterizes the growth of the cells of that cell culture. If at least one cell culture vessel is movable by a transport device in the incubator the cell cultures of several cell culture vessels can be measured one after the other with a single or with few measurement devices. It is also possible to provide for several or a multitude of measurement devices for observing the growth of several cell cultures in parallel.

The measurement device can furthermore be mountable to a transport device. The measurement device can be mountable or be mounted to a positioning mechanism, with which the measurement device is movable and positionable. The positioning mechanism can comprise a movable robotic arm and is preferentially electrically controllable, in particular by a control program of the control device. In this way, the growth of the cells of several cell culture vessels can be measured one after another with one or with several measurement devices one after another. The positioning mechanism can be designed as a part that can be inserted into the incubator chamber. The energy supply of this part can be established by a cable connection with the incubator, preferentially by a cable that is fed through an opening of the wall, e.g. a port, or by such a cable connection to an external voltage source. The control device can be configured to control the positioning mechanism in function of cell monitoring data.

Also the temperature control device can be understood as a handling device with which the atmosphere on the inside of the incubator chamber is regulated to the desired value, in particular 37° C. The term temperature control refers to the raising or lowering of the temperature of the atmosphere by heating or cooling. Preferentially, the temperature on the inside is adjusted by a temperature change of the walls of the incubator. Temperature sensors of the respective temperature control device are distributed over at least one position inside and/or outside of the incubator chamber, in particular on a wall of the incubator chamber.

The incubator comprises preferentially a user interface device, through which the user can input data to the data processing device, resp. the control device, and/or information can be output to the user. Preferentially, the incubator, resp. the user interface device is configured to allow the user to input at least one operation parameter for the operation of at least one measurement device at this user interface device, resp. to receive information for it. In this way, a single user interface device can be used by the user to influence or to control the incubator and also the at least one measurement device, or to receive information from those. In particular, a measurement device can be configured to display cell monitoring data to the user in response to a request that was carried out by the user via the user interface device. The displayed cell monitoring data can be in particular a confluence, a number of cells, and/or at least one optical image of the at least one cell culture.

A machine-controlled handling of the incubator is preferentially a program-controlled handling, i.e. a handling that is controlled by a program. The program-controlled handling of a sample is to be understood as the process of handling being carried out essentially by working off a number or a multitude of program steps. Preferentially the program-controlled handling is carried out using a least one program parameter, in particular at least one program parameter that has been selected by the user. A parameter selected by the user is also termed as a user parameter. The program-controlled handling is carried out preferentially by means of the digital data processing device that is in particular part of the control device. The data processing device can comprise at least one processor, i.e. a CPU, and/or comprise at least one microprocessor. The program-controlled handling is controlled and/or executed preferentially according to the specifications of a program, in particular of a control program. In particular, essentially no user action is required with the program-controlled handling, at least after the acquisition the program parameters necessary on the user-side.

A program parameter is to be understood as a variable that can be adjusted in a predefined manner within a program or a sub-program, valid for at least one execution (call) of the program or sub-program. The program parameter is defined, e.g. by the user, and controls the program or sub-program and effects a data output in function of this program parameter. In particular, the program parameter influences on and/or controls and/or the data that was output by the program the control of the device, in particular the control of the handling by means of the at least one handling device.

A program is to be understood in particular as a computer program. A program is a sequence of commands, in particular consisting of declarations and instructions, in order to be able to process and/or solve a certain functionality, task or problem on a digital data processing device. In general, a program is available as a software that is used with a data processing device. The program can in particular be available as firmware, in the case of the present invention in particular as firmware of the control device of the incubator or the system. The program is available mostly on a data storage medium as an executable program file, frequently in the so-called machine code that is loaded into the memory of the computer of the data processing device for execution. The program is processed as a sequence of machine commands, i.e. processor commands, by the processors of the computer and by this executed. A computer program is also to be understood as the source code of the program, from which in the course of the control of the laboratory device the executable code can be generated.

A user interface device can be part of an incubator, or a module. A user interface device comprises each preferentially: a control device for the user interface device; a communication device for the establishment of a data connection with a laboratory device, in particular an incubator, via an interface device thereof; an input device for the acquisition of user inputs of one user; an output device, in particular an indicator and/or a display, for the output of information to the user, in particular a touch-sensitive display. With this, the control device of the user interface device is preferentially configured to exchange data with the control device of the incubator via the data connection.

A cell culture vessel is in particular fabricated of plastic, in particular PE or PS and comprises in particular a planar base plate, which constitutes the growth surface. This can comprise a surface treatment for the promotion of the adhesion of cells. The cell culture vessel can be closable resp. equipped with a PE cap or a gas-exchange cap, in particular with a lid with an optionally contained filter. In particular, the cell culture vessel is stackable. Particularly suited is a cell culture bottle of Eppendorf.

The invention relates in particular to a data exchange system comprising at least an incubator according to the present invention and at least one external data processing device, where the at least one incubator and the at least one external data processing device are configured for the data exchange via a data connection, and in particular exchange cell monitoring data. With this data exchange system it is possible to design in particular the data acquisition effectively in order to acquire data from a number of a multitude of incubators according to the present invention, in particular to acquire centrally by means of an external data processing device. The external data processing device can be configured to gain reference data on the growth of a cell type or cell line in function cell monitoring data from a multitude of acquired cell monitoring data via at least one statistical method, in particular for determining for certain growth goals of that cell type or cell line the dependencies on certain first or second measurement value resp. cell monitoring data.

The invention relates in addition to a system for the monitored growth of cell cultures, comprising: at least one incubator comprising:—an incubator chamber for accepting at least one cell culture vessel, which contains a cell culture growing therein, a sensing device for the measurement of at least one chamber parameter that characterizes the physical state of the incubator chamber in for of at least one first measurement value, at least one measurement device for the measurement of at least one growth parameter that characterizes the growth of the cells of the cell culture in form of at least one second measurement value, in which the system comprises furthermore:—a data storage device and—a data processing device that is configured for the acquisition of the at least one first measurement value and the at least one second measurement value in form of cell monitoring data and for the storage of the cell monitoring data in the data storage device. That means that the acquisition and the combination of the first and second measurement values does not necessarily occur in the incubator but in the external data processing device of the system, which is not part of the incubator. In this way, in particular the cell monitoring data acquired by several incubators that have a data connection in a laboratory network or the network of laboratory devices of a company can be collected and stored centrally by the external data processing device.

The invention relates moreover to a method for the monitoring of the growth of at least one cell culture in an incubator, comprising the steps: Measuring at least one chamber parameter of the incubator chamber of the incubator, in which the chamber parameter characterizes the physical state of the incubator chamber in form of at least one first measurement value by means of at least one sensing device of the incubator, measuring at least one growth parameter that characterizes the growth of the cells of this cell culture in form of at least one second measurement value by means of at least one measurement device of the incubator, acquiring of the at least first measurement value and the at least second measurement value in form of cell monitoring data by means of a data processing device of the incubator or of a system and storing of the cell monitoring data by means of a data storage device of the incubator or of a system, in which the system comprises this incubator. Another optional step of the process consists in executing at least one process step of the incubator in function of cell monitoring data. The process according to the present invention is preferentially executable by the incubator or system according to the present invention. The process according to the present invention is preferentially provided as program code that effects the aforementioned steps if the program code is executed on the data processing device of the incubator or system according to the present invention. The incubator or system according to the present invention is preferentially configured to execute the process or program code according to the present invention.

Additional preferred embodiments of the method according to the present invention can be found in the description of the incubator according to the present invention and its preferred embodiments. Furthermore, other embodiments options of the invention follow from the embodiment examples in the figures.

Figure 1A:
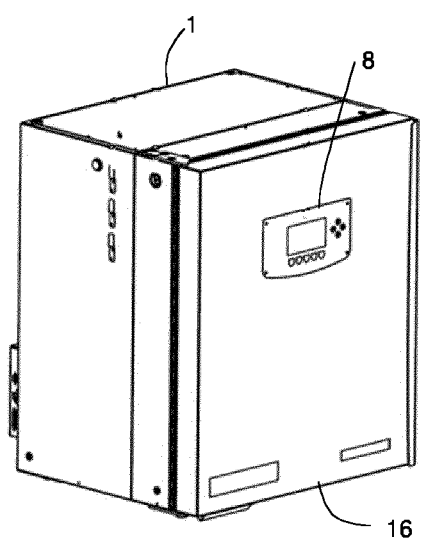
FIG. 1a illustrates a perspective view of the front of an incubator according to the present invention corresponding to an exemplary embodiment
Figure 1B:
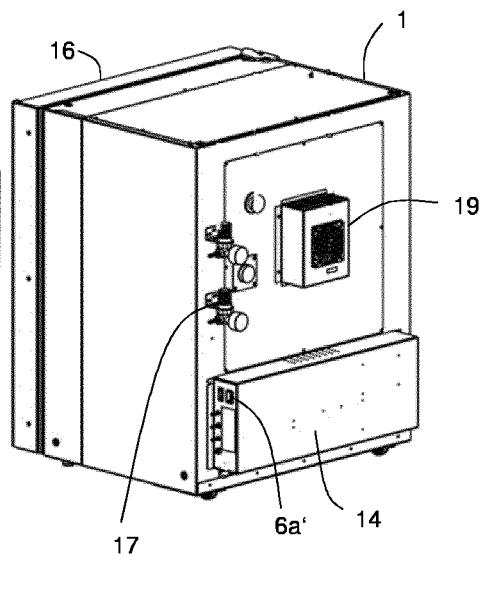
FIG. 1b illustrates a perspective view of the back of the incubator of FIG. 1A
Figure 2:
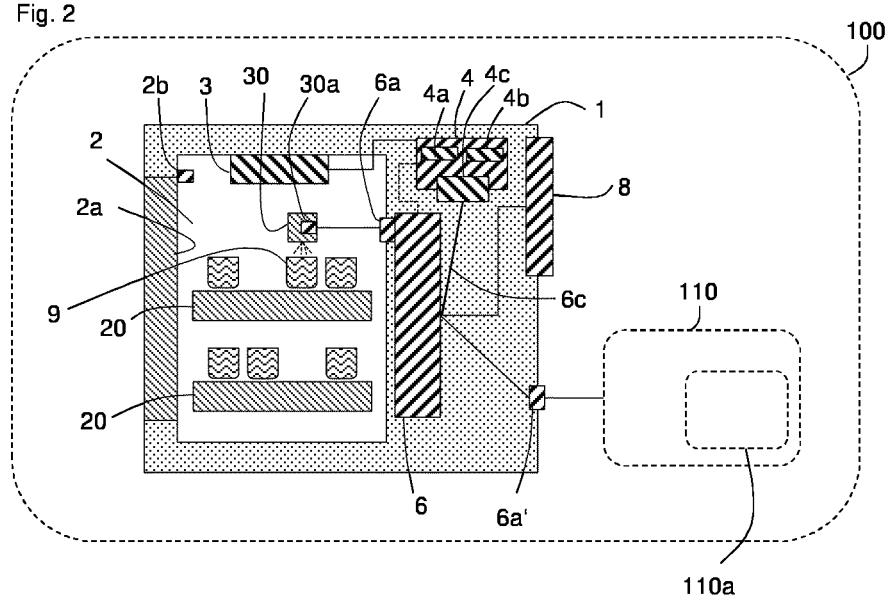
FIG. 2 illustrates a schematic view of an incubator according to the present invention corresponding to another exemplary embodiment.

FIG. 1a illustrates the incubator 1 for the monitored growth of cell cultures, here a CO2 incubator for the growth of eukaryotic cells. The incubator comprises: an incubator chamber 2 (see FIG. 2) for accepting at least one cell culture vessel 9, that contains a cell culture growing therein, a sensing device 3 for the measurement of the chamber parameter temperature, relative concentration of CO2 gas, and relative air humidity. The values of these chamber parameters are read in regularly by the control program of the control device 4 of the incubator as first measurement values. The incubator 1 furthermore comprises a measurement device 30 for the measurement of the growth parameter "confluence of the cell layer in the cell culture vessel" as second measurement values. This is carried out by illuminating and detecting the cell layer, resp. optionally imaging the cell layer, triggered by the control device 4 in regular time intervals. The images of the cell layer are analyzed by the data processing device of the control device 4 through software-based image analysis methods and the cell density is determined.

Here, the measurement device 30 is a network instrument that linked by a plug connector 6a of the Ethernet switch 6 of the incubator in a data connection with the control device, resp. its Ethernet adapter 4c The cell culture vessels 9 are arranged on shelf plates 20. The incubator chamber 2 is accessible via the incubator door 2a. The opening of the incubator door can be acquired by the sensor 2b of the control device.

The control device 4 comprises a data storage device 4a, and a data processing device 4b that are configured for the acquisition of the at least one first measurement value and the at least second measurement value in form of cell monitoring data and for the storage of cell monitoring data in the data storage device.

In this way, the incubator 1 collects the information about the growth of the cells in the incubator chamber 2 and thus gains reference data that allow for a standardized approach for the cell culture in the incubator. The high-quality and precisely calibrated sensors 3 of the incubator offer the basis for the collection of a reliable data set for the characterization of the cell growth in that incubator. In doing so, the internal parameters of the incubator, in particular chamber parameters, together with the growth parameters measured by the measurement device are collected so that a determination of potential correlations between the parameter values and their changes is rendered possible. In this way, cell monitoring data is collected in the incubator, and these cell monitoring data can be used as reference data for the development of cell cultures growing in the incubator in the future.

In the cell culture with eukaryotic cells, users work in $CO_2$ incubators. In the state of the art, a reproducible behavior of these cells in test systems is frequently supported by subjective impressions from morphological controls or end point determinations (cell counting). Additionally, no automatic documentation of the results of the cells in the incubator is carried out in conjunction with the environmental conditions, which the incubator 1 makes available directly. The classical microscoping of the cultures does not cover a complete monitoring of the cells but represents only snap shots. Additionally they in most cases do not provide quantifiable information. This cell counting in the state of the art is a disruptive process that does not occur during the growth.

Moreover, the incubator 1 is configured to execute by means of the control program of the control device 4 a planning program that predicts the temporal evolution of the growth (confluence) from the cell monitoring data and known reference data and that shows to the user in the display, via the user interface device 8, the information about the reaching of the desired growth goal, here a confluence as specified by the user.

Moreover. the cell monitoring data is transferred optionally from the incubator, resp. its control device via an Ethernet interface 6a' to an external data processing device 110, which also, if applicable, collects and stores the cell monitoring data of further incubators (not shown) of the same network 100. Thereby, the cell monitoring data are combined centrally in the external device and analyzed statistically in order to obtain reference data for the standard growth of a certain cell type of cell line.

In an alternative embodiment of the invention, the acquisition of the first measurement values is carried out together with that of the second measurement value, resp. their combination in form of cell monitoring data does not occur in the data processing device 4b of the incubator but in a second, external data processing device 110. In this way, the measurement device 30 can, in particular independently form the incubator 1 or its control device 4, transfer the second measurement values to an external data processing device 110, in particular with a time stamp of the measurement, and the control device 4 can transfer the first measurement values that have been measured by the sensing device 3 to an external data processing device 110, in particular with a time stamp of the measurement. The data processing device 110 forms the cell monitoring data from the first and second measurement values and stores them. The stored cell monitoring data or the reference data obtained from it by the data processing device 110 is made available again to the network instruments of the network, in particular to the incubators. In this way, a data exchange system resp. a system according to the present invention is provided, with which it is possible to achieve the reaching of growth goals in a standardized manner.

Figure 3:
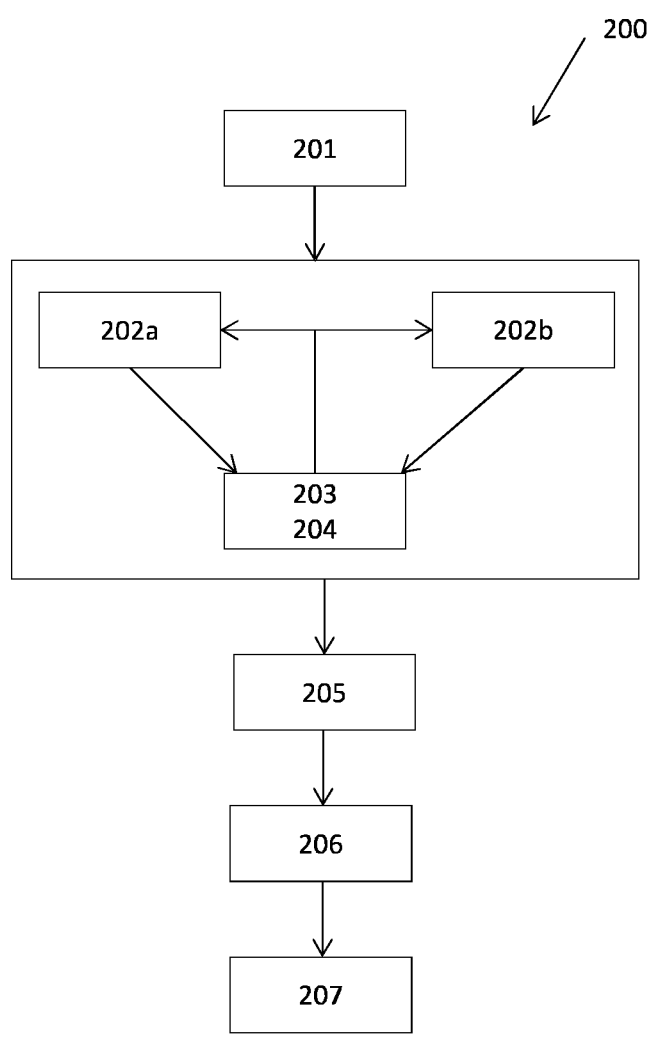
FIG. 3 illustrates schematically the process according to the present invention corresponding to exemplary embodiment.

The method 200 for the monitoring of the growth of at least one cell culture in an incubator, as illustrated in FIG. 3, comprises the steps:

Method for the monitoring of the growth of at least one cell culture in an incubator, comprising the steps:

Registration of a growth goal that is specified by the user via the user interface device, e.g. a desired confluence, in particular for one cell line clearly specified by the user (201).

Measuring at least one chamber parameter of the incubator chamber of the incubator, in which the chamber parameter characterizes a physical state of the incubator chamber, in form of at least one first measurement vale, by means of at least one sensing device of the incubator (202a).

Measuring at least one growth parameter that characterizes the growth of the cells of that cell culture, in form of at least one second measurement value, by means of at least one measurement device of the incubator (202b).

Acquisition of the at least one first measurement value and the at least one second measurement value in for of cell monitoring data by means of a data processing device (203) and analysis of the cell monitoring data (204), here by comparison with known reference data.

Repetition of the steps 202a, 202b, 203, 204 until the growth goal is reached, resp. until the cell growth is terminated by the users.

Storing of the cell monitoring data by means of a data storage device (205).

Definition of new reference data on the basis of the cell monitoring data (206).

Providing the new reference data to the incubator for the future incubation (207).

The monitoring of cell in the incubator 1 and considering the movement and the disturbance of the cell cultures during the growth is part of the functions of the incubator 1 and can be control by it. Furthermore, the environmental conditions (first measurement values) are connected to the cell results (second measurement values) and optionally documented. It is thus possible to quickly and easily standardize the growth behavior of cells A CO2 incubator is equipped with a measurement station 3, which automatically records information about the growth of cells (confluence and optionally cell number). This information is directly stored in the incubator 1 or by the system and is thus available in the incubator in addition to the information about the environmental conditions (first measurement values).

Further methods are beneficial for optimizing the standardization of the cell culture with such an incubator, resp. system:

After the thawing process of cells the user can request to determine the time until all or a specified fraction of the cells has adhered to the surface of a cell culture vessel. The user receives an information at that moment. The deviation from known standard values is preferentially signaled to the user or stored as data.

The user receives an information on the amount of cells that are present in adhered form after the seeding or thawing. With the total number of cells being specified, also the survival rate could be determined. The user receives a message when his desired confluence of the cells is reached, for example for manipulating the cells, and can compare this value with those that have already been stored, in order to achieve a standardization.

The user can request to automatically determine, starting from a specified number of measured sample, spectra resp. reference ranges, in which the typical measurement values of a cell lines are located, The user can use the incubator for monitoring the growth of cells. He can control the measurement device 30 directly at the operating device 8 of the incubator and document the results of the cell growth and the environmental conditions as well as the event-log of the incubator in a combined for—preferentially, this is carried out automatically. As the results are provided as stored directly in the incubator, the growth curves can be acquired in a standardized form. If the user specifies his cell type, the current growth curve is compared directly with historic data and documented. The user can request to automatically to have the deviation evaluated by an analysis algorithm as good or bad. In case of deviations from the expected results the user can act immediately and document that later. With the measurement device 30 being part of the incubator an unambiguous acquisition of the environmental conditions of the cell culture is guaranteed.

Additionally, the incubator 1 is optionally integrated into a network 100 and sends the first and second measurement values to a data base on an external data processing device. If the incubator, resp. the system stores these cell monitoring data, they are available to all users of the network. If the cell monitoring data are stored e.g. in a cloud they can be made available to all users of the global network. Thus, combined cell and environmental conditions data can be transferred automatically from work group to work group across the whole world. This is particularly beneficial as the cooperation between users in the in the scientific sector is very important. The more the cell monitoring data resp. the reference data are valid and the results become more traceable, the easier and faster a collaboration in this field leads to reliable results. The cell culture is known for the standardization of methods and the reproducibility of results being essential and at the moment not being optimal. A global data base of combined cell data and environmental conditions data that are determined reliably as cell monitoring data according to the present invention as they are based on reliable incubator data, allows for an efficient transfer of protocols and results.

The invention claimed is:

1. An incubator (1) for the monitored growth of cell cultures comprising
    an incubator chamber (2) for accepting at least one cell culture vessel (9), which contains a cell culture growing therein, wherein the incubator chamber (2) comprises chamber walls, at least one chamber door (2a) and at least one chamber opening, which is closable by the at least one incubator door and through which the cell culture vessels (9) can be placed in the inside or removed from the inside of the incubator chamber,
    a sensing device (2b; 3) for the measurement of at least one chamber parameter, which characterizes the physical state of the incubator chamber, in form of at least one first measurement value, which includes a time stamp, and the sensing device (2b) is configured to record the opening and/or closing of the incubator door as a chamber parameter in form of the at least one first measurement value,
    at least one measurement device (30) for the measurement of at least one growth parameter, which characterizes the growth of the cells of this cell culture, in form of at least one second measurement value, which includes a time stamp, wherein the measurement device is a cell-counting device and the growth parameter describes the number of cells in a test area of the cell culture vessel (9);
    a data storage device (4a) and a data processing device (4b), which is programmed to acquire and collect the at least one first measurement value together with the at least one second measurement value in form of cell monitoring data, and which is programmed to store the cell monitoring data in the data storage device and to generate an electronic documentation file, which is stored in the data storage device and in which the growth of multiple cell cultures in cell culture vessels is logged and documented in the form of time-dependent cell monitoring data, for providing the stored cell monitoring data as reference data for the estimation of the development of cell cultures growing in the incubator in the future,
wherein, in order to detect a correlation, the data processing device (4b) is programmed to acquire and store the at least one first measurement value and the at least one second measurement value simultaneously as a function of time, and wherein the at least one first measurement value and the at least one second measurement value, which are simultaneously stored as a function of time, are present in the incubator forming one unique device.

2. The incubator according to claim 1, in which the data processing device (4b) of the incubator controls the execution of the measurement of at least one second measurement value.

3. The incubator according to claim 1, further comprising a measurement device for the measurement of a growth parameter selected from the group comprising:
confluence of the cell layer in the cell culture vessel, morphology of the cells of the cell layer, and cell adhesion.

4. The incubator according to claim 1, in which the incubator and/or its data processing device (4b) and/or a control device (4) of the incubator and/or the at least one measurement device (30) is configured to acquire cell monitoring data corresponding to at least one of the following configurations:
cell monitoring data is acquired according to a schedule that can be defined by the incubator and/or can be influenced or defined by the user via a user interface device of the incubator; and/or
cell monitoring data is acquired at defined intervals that can be defined by the incubator and/or influenced or defined by the user via a user interface device of the incubator.

5. The incubator according to claim 1, in which the incubator and/or its data processing device (4b) and/or a control device (4) of the incubator and/or the at least one measurement device (30) is configured to acquire the cell monitoring data as a function of at least one specified event selected from the group comprising:
a first measurement value measured by the sensing device fulfills one specified condition; optionally wherein the specified condition is an illicit deviation from the set temperature in the incubator chamber, which could be caused by an open incubator door; or an illicit deviation from a relative gas concentration in the incubator chamber, represented by a CO2 and/or O2 value; or a specified number of openings of the door in a specified time interval; or an illicit deviation from an air humidity;
an error condition that has been identified by the incubator, regarding hardware or software;
a control signal received via a communication device of the control device of the incubator or of the measurement device that triggers the acquisition of cell monitoring data; such control signal can be prompted by an external data processing device or be prompted by an user input.

6. The incubator according to claim 1, in which the incubator and/or its data processing device (4b) and/or a control device (4) of the incubator and/or the at least one measurement device (30) is configured so that a control program executed by the data processing device or the control device of the incubator and/or the at least one measurement device triggers a measurement of cell monitoring data after an analysis method employed by the control program had analyzed previously measured second measurement values.

7. The incubator according to claim 6, in which an analysis program provides the triggering of the measurement of cell monitoring data due to a fulfilled condition, which can be selected from the group comprising:
at least one previously measured second measurement value deviates from at least one reference value;
at least one trend of two or many previously measured second measurement values deviates from at least one reference trend.

8. The incubator according to claim 1, in which the incubator comprises a user interface device (8), through which both the incubator as well as the at least one measurement device is controllable by the user.

9. Data exchange system comprising
at least one incubator (1) according to claim 1 and
at least one external data processing device (110),
in which the at least one incubator and the at least one external data processing device are configured for the data exchange via a data connection; wherein the data comprises cell monitoring data.

10. Method for the monitoring of the growth of at least one cell culture in an incubator according to claim 1, comprising the steps:
measurement of at least one chamber parameter of the incubator chamber of the incubator, in which the chamber parameter characterizes a physical state of the incubator chamber, in form of at least one first measurement value by means of at least one sensing device of the incubator (202a);
measurement of at least one growth parameter that characterizes the growth of the cells of that cell culture in form of at least one second measurement value by means of at least one measurement device of the incubator (202b);
acquisition of the at least one first measurement value and the at least one second measurement value in form of cell monitoring data by means of a data processing device (203); and
storage (205) of the cell monitoring data by means of a data storage device.

11. The method according to claim 10, further comprising execution of a work step of the incubator as a function of the cell monitoring data.

12. The method according to claim 10 or 11 further comprising determination of a correlation between cell monitoring data represented by first and second measurement values and storage of the information about that correlation.

13. The method according to claim 11, in which the work step provides that a planning program for the calculation of a growth goal is executed by the data processing device.

14. The method according to claim 11, in which the work step provides that the time of reaching a growth goal as being calculated by the data processing device (4b; 110a) in function of the cell monitoring data is indicated to the user on the user interface device (8) or output differently.

* * * * *